United States Patent [19]

Schouenborg

[11] Patent Number: 5,131,274
[45] Date of Patent: Jul. 21, 1992

[54] METHOD AND APPARATUS FOR TESTING EGGS FOR CRACKS OR HOLES

[75] Inventor: Kurt O. P. Schouenborg, Roedovre, Denmark

[73] Assignee: Terpa Poultry B.V., Amstelveen, Netherlands

[21] Appl. No.: 689,658

[22] Filed: Apr. 23, 1991

Related U.S. Application Data

[63] Continuation of Ser. No. 492,371, Mar. 9, 1990, abandoned, which is a continuation of Ser. No. 206,450, Jun. 14, 1988, abandoned.

[30] Foreign Application Priority Data

Jun. 18, 1987 [DK] Denmark ............................. 3118/87

[51] Int. Cl.$^5$ ...................... G01N 29/12; A01K 43/00
[52] U.S. Cl. ........................................ 73/595; 73/12; 73/579; 209/510
[58] Field of Search ................... 73/595, 579, 12, 79; 209/510

[56] References Cited

U.S. PATENT DOCUMENTS

| | | | |
|---|---|---|---|
| 3,067,605 | 12/1962 | Bliss | 73/595 |
| 3,503,501 | 3/1970 | Seaborn | 73/595 |
| 4,744,299 | 7/1973 | Bliss | 73/595 |

FOREIGN PATENT DOCUMENTS 8603208 7/1987 Netherlands ..................... 209/510

*Primary Examiner*—John E. Chapman
*Attorney, Agent, or Firm*—Sprung Horn Kramer & Woods

[57] ABSTRACT

A procedure and apparatus is provided for the examination of eggs to determine the presence of cracks or holes in the egg shell through the examination of the resiliency of the shell. This procedure and apparatus are characterized by the subjection of the egg to an examination cycle which consists in exercising intermittent pressure on at least a section of the egg shell by a movably mounted probe to create a series of in principle elastic deformations, where each subsequent deformation in the series is caused by the shell's action on the probe as a reaction to the immediately preceding deformation. This is done through subjecting the probe, from its original position at a distance from the shell, to a continuous force directed at the egg's shell, forcing the probe down to strike against the shell, and this results in an elastic deformation of same, whereupon the resilience of the egg shell causes it to return to its original shape, throwing back the probe, whereafter the probe, again as a result of the continuous force, is brought to strike against the shell once more before again being thrown back. This action is repeated several times, with decreasing oscillations, so that the probe's action seen as a whole is a bouncing movement against the egg shell. This movement is in principle observed as a decreasing oscillation, in connection with which the amplitude and duration of each of the probe's oscillations is measured, preferably electrically, and the number of oscillations from which the amplitude and duration exceed preset parameter values is counted and registered electronically, whereupon the above cycle is repeated a given number of times (n), and distributed evenly around the egg's axis of symmetry. The lowest registered number of ocilllations from the (n) examination cycles is registered against an empirical parameter.

19 Claims, 4 Drawing Sheets

METHOD AND APPARATUS FOR TESTING EGGS FOR CRACKS OR HOLES

This application is a continuation of application Ser. No. 07/492,371, filed Mar. 9, 1990, and now abandoned which is a continuation of application Ser. No. 07/206,450, filed Jun. 14, 1988 and now abandoned.

BACKGROUND OF THE INVENTION

The present invention relates to a procedure for examining eggs to determine the presence of cracks or holes in the shell through an examination of the elasticity of same.

For many years, a great deal of work has been put into developing suitable methods and apparatus for the automatic detection of so-called cracked eggs, i.e. eggs with cracks or holes in their shells.

Such detection is important for several reasons. One is that the storing quality of such eggs is reduced and their use as food may entail a health risk. Another reason is that damaged eggs cause loss, and irritation in the further handling and distribution of these eggs.

In a number of instances, attempts have been made to base detection on the examination and measurement of several conditions in connection with vibrations or oscillations in the egg shell. Thus, for instance, a method is described in U.S. Pat. No. 3,503,501 whereby a continuously vibrating probe is vibrated against the egg, and the resistance and oscillations, as well as the phase differences between the probe's oscillations and the oscillations produced in the egg's shell during the rotation of the egg are measured. In U.S. Pat. No. 3,744,299 a method is described in which the eggs are rolled over a number of piezoelectric crystals thus receiving energy impulses, and the process consists partly of measuring the energy impulse returned by the eggs and partly the duration of the impulse. The latter process is then used as a gauge for ascertaining the presence of cracks or holes in the shell. Another method is known from U.S. Pat. No. 3,067,605 in which the recoil of light hammers striking passing eggs is measured. Eggs causing a recoil below a certain dimension are defined as cracked eggs.

However, it has been demonstrated that none of these known methods have provided satisfactory results in practice, so one is still obliged to use the familiar method of inspecting the eggs as they pass over a table with a strong light underneath, a method that is both costly because of the wages involved and is also encumbered with the uncertainty involved in such enervating inspection work.

SUMMARY OF THE INVENTION

The object of the present invention, therefore, is to present a new procedure, along the lines indicated in the introduction, which will be suitable for the fully-automatic detection of cracked eggs and which will have a low margin of error.

The procedure in the present invention is unique in that the egg is subjected to an examination cycle consisting of the exertion of a series of shock-like elastic deformations on at least one section of the egg shell. These deformations are caused by an elastically suspended probe. Each subsequent deformation in the series is a result of the shell's action on the probe as a reaction to the immediately preceding deformation. In this cycle, the elastically suspended probe is subjected to continuous pressure towards the shell from its point of suspension some distance above the shell. Said pressure forces the probe down to strike the shell, and causes an elastic deformation of same. The elasticity of the shell causes it to return to its original shape, and as it returns to its original state, it forces the probe back. The continuous pressure again forces the probe to strike against the egg shell, before it is once again forced back by the shell's reaction. This procedure is repeated several times, with decreasing oscillations, so that the probe's action can be described as a bouncing movement against the egg shell, mainly as a detectable damped oscillation in which the amplitude and duration of each of the probe's oscillations is measured, preferably electrically. At the same time the number of oscillations is counted and registered electronically in order to ascertain whether amplitude and duration exceed preset parameters. Thereafter the egg is rotated on its axis of symmetry and the above cycle is repeated a given number of times (n), distributed equally around the axis of symmetry of the egg. The lowest number of registered oscillations from the (n) examination cycles is then compared with an empirical tolerance value. This procedure utilizes the fact that a section of egg shell without cracks or holes has a higher degree of elasticity than a section with a crack or hole, and that this section therefore after a certain amount of elastic deformation, will result in both more and larger oscillations of the probe than will a section with cracks or holes. Through the procedure described above, it has thus proved possible to achieve a degree of detection which is fully equal to, and often considerably better than, the rate of detection achieved through the traditional inspection of the eggs during their passage along a lit conveyor belt. At the same time, the results of the measurements obtained from the above procedure can be read off a computer, so that it is possible to obtain both an automatic and a direct statement of the shell quality of the individual egg, a statement which in turn can be used in order to direct the control of a sorting mechanism.

The procedure is thus also suitable for use at very high speeds, so that it can be used in connection with the inspection lines generally available in egg packaging plants, in which the egg is continuously rotated around its axis of symmetry- during the examination process.

When several parallel examinations are carried out concurrently, each on its own section of the shell and along the axis of symmetry of the egg, and the number of oscillations are counted and registered individually for each section, the lowest value among the (n) examination cycles x the number of sections is compared with the limits of tolerance. Thus a particularly thorough examination of all the sections of the shell can be achieved, so that there will be a high degree of certainty that any crack present in the shell will be revealed.

Through the procedure embodied in this invention, it is possible to transform the damped oscillations of the probe by means of a transducer consisting of a piezoelectric, optical, magnetic or capacitative device, into an electrical signal. This signal can then be converted via an amplifier, a comparator and a signal re-shaper to straight digital counting impulses. These impulses can in turn be transferred via a counter and stored in a computer alongside the results from the other examinations of the egg. With the aid of the computer program it is then possible to ascertain the lowest value for the number of bouncing oscillations in an examination cycle. These figures can then be compared with the empirical parameters, so that the results of all the measurements carried out on an egg are assessed automatically as a whole.

In a procedure particularly preferred in accordance with the invention, a probe consisting of a hard tube or rod-shaped device, such as a glass tube, is used. This tube is elastically suspended in a holder, and the holder is subjected to the effects of a spring, preferably a laminated spring, which seeks to retain the tube in a fixed position in relation to a base, and at a distance above the egg. The effects of a pulsating pressure in a pressure chamber is used to force the tube down to strike the egg shell. The area of the tube that is made to bounce against the shell is preferably to lie between 15% and 35%, optimally between 20% and 30%, of the total length of the rod measured from its freely protruding end. Thus the probe will give a particularly effective indication of the elasticity of the shell as the chosen design and suspension of the probe and the experimental area chosen achieves a suitably small damping of the oscillations produced by the movements of the shell. At the same time, it becomes possible to adjust the amount of pressure used to force the probe down towards the egg in a simple manner by adjusting the pressure in the pressure chamber.

The invention also comprises an apparatus to carry out this procedure. This apparatus is unique in that it comprises a support for the egg, as well as revolving rollers that can rotate the egg around its axis of symmetry, and an elastically swung probe suspended in a holder, preferably located above the egg, as well as devices for moving the holder so that the probe can be brought to strike against the egg in order to cause an elastic deformation of the shell, allowing the probe to bounce on the shell. Furthermore, a transducer, such as a piezoelectric, an acoustic, an optical, a magnetic or a capacitative device, is to be fitted between the probe and the holder in order to transfer the bouncing movement of the probe to an electrical signal. In addition, an amplifier, a comparator, a signal re-shaper such as a one-shot multivibrator, a counter, and a computer are used in order to process the electrical signal from the transducer. Thus an apparatus is obtained which by simple means can automatically detect the presence of cracks or holes in the shell of an egg. Through the computer program, the results of this detection can be used as a statement on the quality of the shell and can be compared to a reference value. Furthermore, the apparatus is suitable for use in connection with a normal inspection line in an egg packaging plant.

Through a preferred embodiment for the apparatus according to the invention, the probe is made of a tube or rod-shaped hard substance, such as a glass tube, one end of which is fitted to a holder between rubber chocks which fix and spring the tube vertically and horizontally. This tube is preferably to be adjusted so that the area which strikes the egg shell lies at a distance of between 15% and 35%, and optimally between 20% and 30%, of the total length of the glass tube from its freely projecting end. Thus a suitable movement of the probe is ensured so that it can react easily to movements in the egg shell when struck against shell with a light pressure.

It is also appropriate to attach the piezoelectric, optical, acoustic, magnetic or capacitative device between the fixed end of the glass tube and the holder, so that it is easily protected during use. However, the said device can also be attached to other places on the glass tube.

In a practical embodiment of the apparatus in accordance with the invention, the holder is in principle u-shaped, with the glass tube orientated in principle at a right angle to the sides of the holder, and besides which, the mass of the glass tube is insignificant compared to the mass of the holder. This results in the own oscillation figure of the holder being far below the oscillation figure of the glass tube, so that good and unambiguous signals are received from the transducer.

A particularly suitable and easily controlled movement of the holder with the glass tube is obtained when the holder is fitted to a base with the help of a stiff spring, particularly a laminated spring. An elastically deformable air pressure chamber is also fitted between the holder and the base. This air pressure chamber is linked to an air pulsator and a vacuum escape valve constructed between the air pulsator and the air distributing chamber via an air distributing chamber built into the base, so that a deformation of the air pressure chamber through a change in the air pressure results in a deformation of the spring, thus causing the glass tube to move towards or away from the egg.

The apparatus described in the invention is particularly practical when there are several holders, each with its own probe, arranged so that the probes all touch their particular section of the egg shell simultaneously, and in which the air pressure chambers for the individual holders are linked by the same air distribution chamber, so that the various probes can be activated simultaneously in a simple manner.

From the preliminary investigations it appears that suitable materials for the probe are relatively light, preferably tube-shaped or rod-shaped blanks of a hard, resilient material such as glass, making it possible to achieve great rigidity and strength combined with a suitable dimension and little mass. At the same time, the area of the probe that is brought into contact with the egg shell should preferably be at such a distance from the probe's freely projecting end that the forces acting on the probe as far as possible balance each others, i.e. The bearing forces at the point of attachment for the probe are as small as possible, so that the deflection of the probe is reduced as little as possible. However, the present invention is not limited to the use of the above-mentioned materials or configurations, but can be extended to any form of probe that can be used for the transfer of the movements stated in the requirements.

Some embodiments of the apparatus according to the present invention will now be described by way of example, with reference to the accompanying drawing, in which

DETAILED DESCRIPTION OF THE INVENTION

Figure 1:
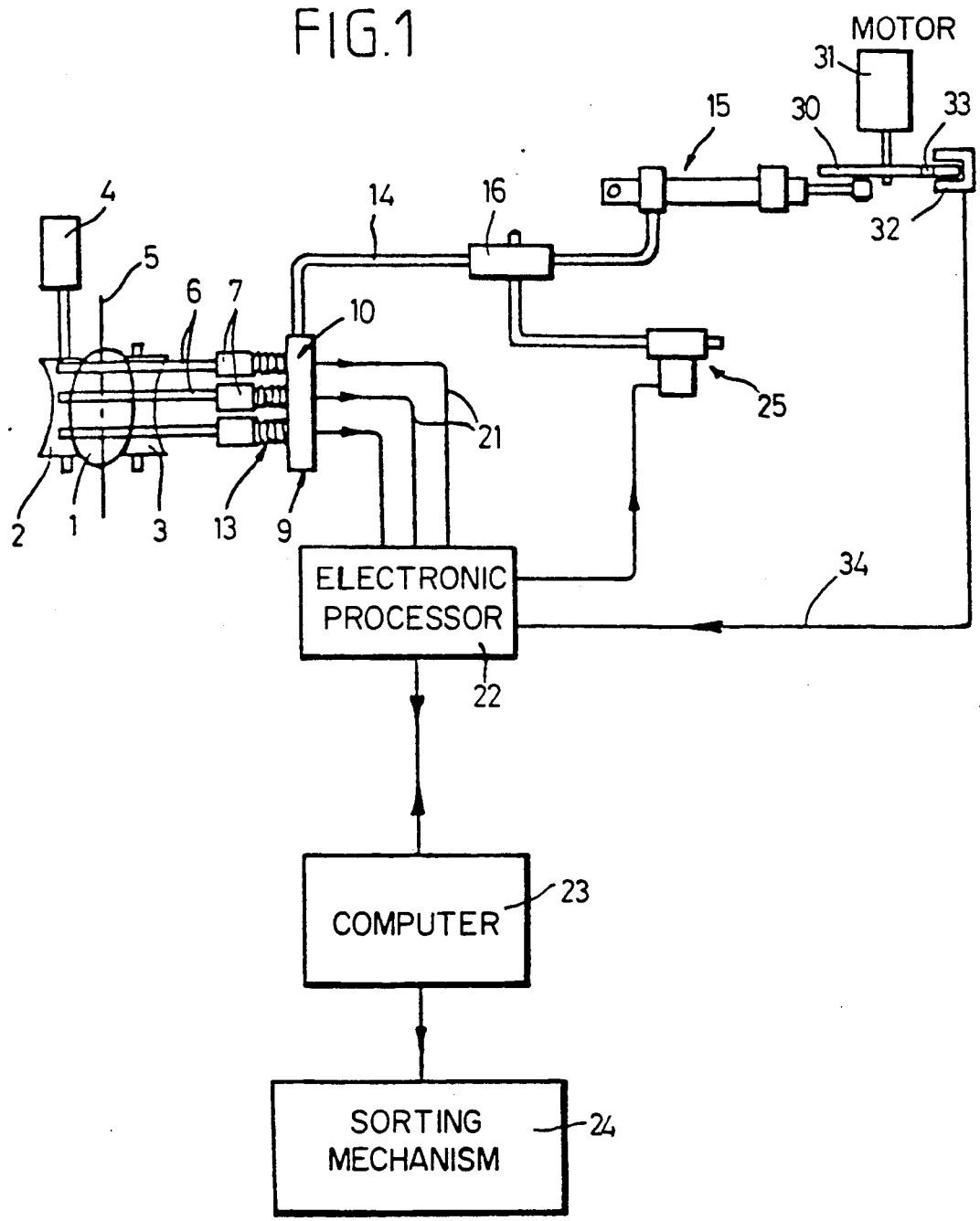
FIG. 1 diagrammatically shows a first embodiment of an apparatus according to the present invention.
Figure 2:
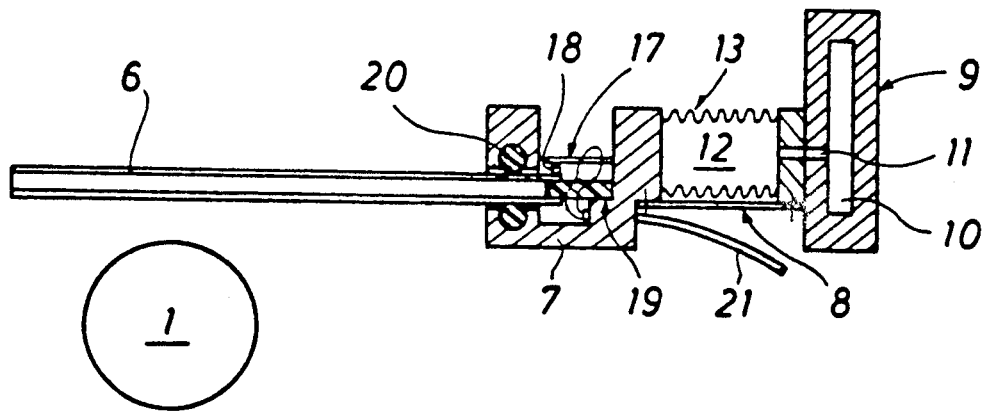
FIG. 2 shows in more detail a first embodiment of a probe with its holder and driving mechanism, as well as the transducer in the shape of a piezoelectric device.
Figure 3:
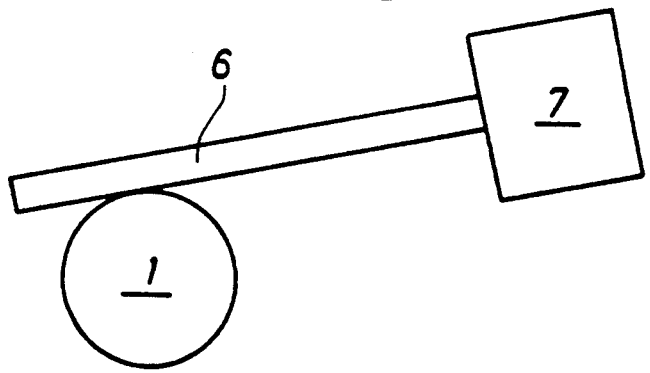
FIG. 3 shows diagrammatically the probe's position while measurements are being taken.
Figure 4:
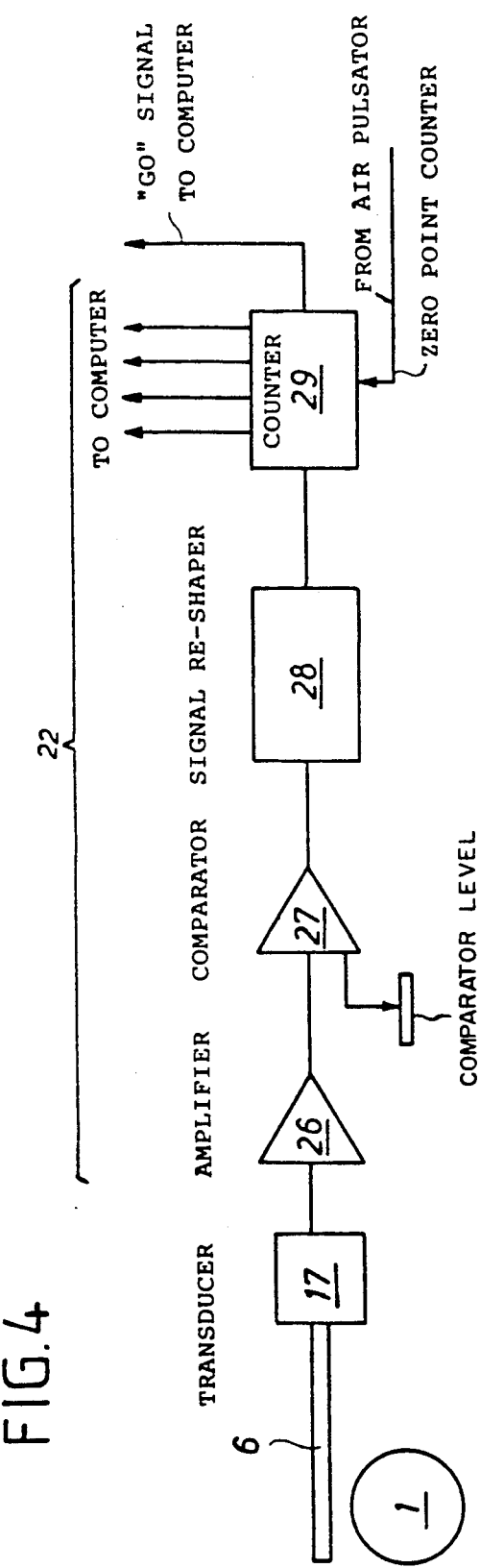
FIG. 4 shows also diagrammatically the electronic system of the apparatus.
Figure 6:
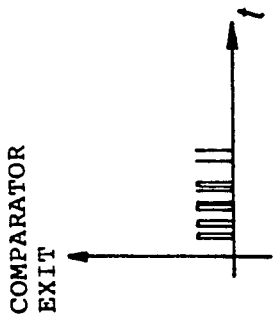
FIG. 6 shows the output signal form the comparator corresponding to the input signal in FIG. 5.

In the embodiment in FIGS. 1, 2 and 3, an apparatus according to this invention is shown for the examination of a single egg 1. This consists of a base comprising two closely placed, rotating rollers with parallel shafts 2, 3, which by means of a motor 4 can be made to revolve in the same direction so that an egg 1 placed onto the rollers is made to rotate mainly around its own longitudinal axis of symmetry 5. Over the egg 1 there are three probes in the form of glass tubes 6. Each glass tube 6 is elastically fixed into a holder 7 at one end, and this holder is attached to a base 9 common to all three holders by means of a laminated spring 8. The base 9 contains a compressed air distribution chamber 10, which is connected through ducts 11 in the base 9 to individual compressed air chambers 12, each belonging to its own holder 7. The individual chamber 12 is extended between and limited by the holder 7 and the base 9, and is limited between these by rubber bellows 13. The compressed air distribution chamber 10 is linked through a pipe line 14 to a compressed air source 15, shown here as an air pulsator, which is operated by a motor 31 via a crank disc 30. Inserted between the air pulsator 15 and the compressed air distribution chamber 10, there is a vacuum escape valve 16. In the holder 7 for the glass tube 6, a transducer 17 in the form of a piezoelectric device is also fitted, and this is attached at one end to the holder. At the other end it is glued to the fixed end of the glass tube 6 by means of a silicon drop 18 so that the oscillating movement of the glass tube 6 causes deformations of the piezoelectric device 17. The glass tube 6 is resiliently mounted in its horizontal position shown in FIG. 2 by means of a rubber chock 19 fitted to the holder in which the glass tube 6 is fixed, and held flexibly in the holder 7 by means of two rubber chocks 20 so that it can swing through a plane that in principle is situated at right angles to the egg shell upon contact. The upper and lower part of the piezoelectric device 17 is linked to an electronic device 22 described in more detail under FIG. 4 by a two-core cable 21. This device 22 contains a counter 29 for each glass tube 6, and the electronic device is in turn linked to a computer 23 and a sorting mechanism 24. A yoke-shaped photoelectric cell 32 is fitted over the crank disc 30 to interact with an air slot 33 in the disc thus giving a signal to the electronic device 22 when the crank disk 30 is in a particular position. Furthermore, a signal can be transmitted from the computer 23 via the electronic device 22 to a solenoid valve 25 which is connected to the vacuum escape valve 16.

When using the apparatus, the egg 1 is made to rotate around its axis of symmetry 5, and a signal is given to close the solenoid valve 25. Compressed air is then fed from the compressed air source 15 through the pipe line 14 and into the compressed air distribution chamber 10. From here it flows through the ducts 11 into the compressed air chambers 12 linked to each of the three holders 7 by the glass tubes 6. Thus the holders 7 with the glass tubes 6 are inclined as the laminated spring 8 is bent, so that the glass tubes 6 are pressed down to strike against the surface of the egg 1 in the position shown in FIG. 3. The glass tube 6 is held pressed against the egg as long as sufficient pressure is retained in the compressed air chamber 12. At the initial impact of the glass tube against the egg, an elastic deformation of the egg shell appears. As a result of the resilience of the shell, this deformation is corrected, and the glass tube is then thrown back before it once more is pressed down to strike against the egg shell again as a result of the pressure in the compressed air chamber. This new blow again causes a deformation of the egg shell, and the operation is repeated so that the glass tube carries out a bouncing movement against the egg shell. The number and size of the bounces will depend on the elasticity of the shell. In other words, the glass tube 6 will bounce many times on the shell if the shell is whole, but only a few times if there is a crack in or near that section of the shell touched by the glass tube. The bouncing motion of the glass tube is now converted by the piezoelectric device 17 to an electrical signal as an expression of the movements of the glass tube. This electrical signal from each of the three piezoelectric devices 17 is sent through the cables 21 to the electronic device 22 where they are processed. A more detailed description of this is found in connection with the following description of FIGS. 4–7, whereafter the resulting data is read off the computer 23. After the measuring has been concluded, the piston in the air pulsator 15 turns, so that the pressure in the pipe 14 changes to a vacuum which is allowed to escape through the valve 16. In this way, the glass tubes 6 are raised up in relation to the egg by means of the laminated springs 8. At the same time, the air slot 33 in the crank disc 30 is positioned in the yoke-shaped photoelectric cell 32 so that this passes a signal through the cable 34 to the electronic device 22 to reset the counter 29 to zero. The measurement is now carried out a preset number of times (n) evenly distributed on the circumference of the egg, whereby the glass tubes 6 are depressed each time to strike the surface of the rotating egg, only to bounce off again. Each time, the electronic device's three counters register how many times the glass tubes 6 have bounced on the surface of the egg, and between each time, the computer reads these figures. Once the inspection has been completed, the solenoid valve 25 opens up to the atmosphere, and the measurements cease. The total number of measurement results now contained in the computer's memory thus consist of 3 × n counter figures, and these are processed by the computer so that this, by means of its program, will find the lowest value and compare this with a coded empirical parameter. If the processed result is lower than the parameter value, the egg is defined as a cracked egg, and this statement is transferred direct as a signal to a sorting mechanism 24 which automatically rejects the egg in question.

Figure 5:
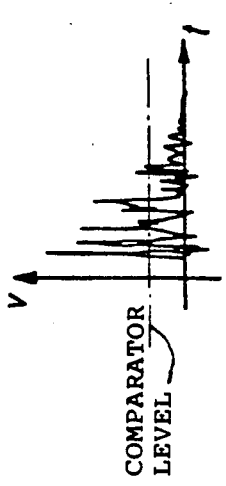
FIG. 5 shows an input signal to the comparator.
Figure 7:
FIG. 7 shows the output signal form the signal re-shaper corresponding to the output signal in FIG. 6.

FIGS. 4–7 show in principle how the electrical signals output from the transducer or piezoelectric device 17 are processed. These signals are sent through an amplifier 26 to a comparator 27, where the current oscillations, in principle sinus-shaped, are detected. An oscillation below a certain size, corresponding to the comparator level shown in FIG. 5, is sorted out, while an oscillation above this size is transferred to a signal re-shaper 28 in the form of the digital impulses shown in FIG. 6, with a length corresponding to the length of the sinus oscillations on the comparator level in FIG. 5, measured in the direction of the time axis t. In the signal re-shaper 28, which may have the form of a one-shot multivibrator, the comparator signal is cleansed of very short impulses, so that the output from signal re-shaper 28 is given the form shown in FIG. 7, with the straight digital counter impulses only containing impulses over a given length. This signal is passed on to a counter 29, which counts the number of impulses in the signal. The counter then passes on a "clear" signal to the computer 23, which subsequently reads the counter 29. When the computer has received all the results of the measurements, the solenoid valve 25 is opened, and the glass tubes 6 are then lifted up off the shell of the egg.

Figure 9:
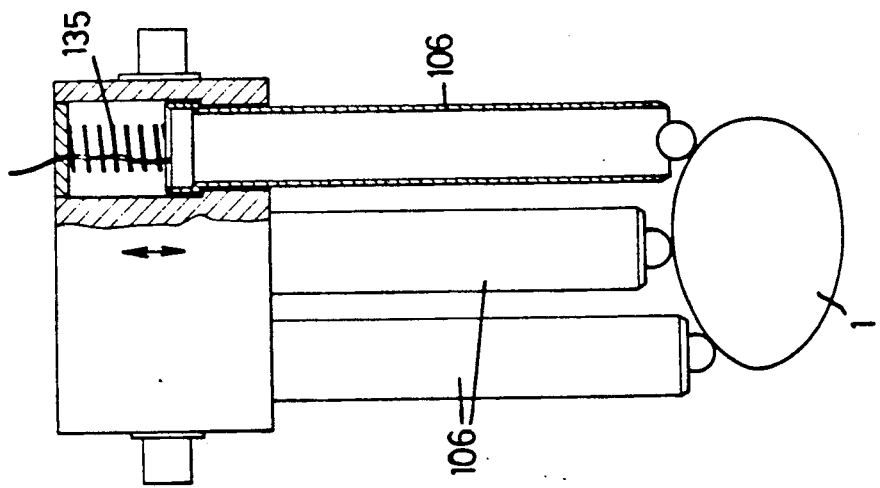
FIG. 9 is a variant of the probe shown in FIG. 8.
Figure 8:
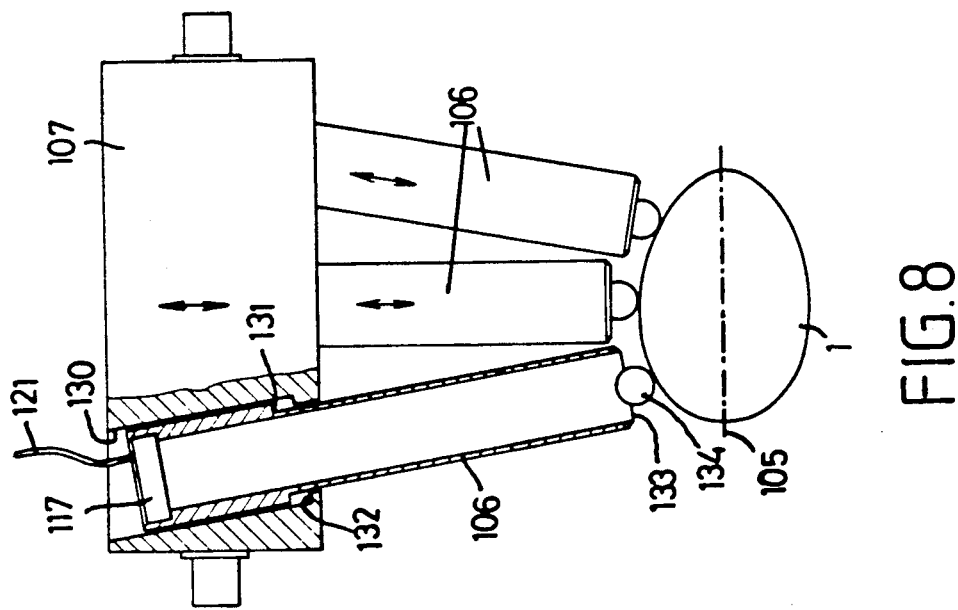
FIG. 8 shows diagrammatically a probe with a ball and an acoustic transducer.

In the embodiments in FIGS. 8 and 9, an apparatus according to the invention is shown for the examination of a single egg 1. As the basic elements in these apparatuses are quite the same as in the apparatuses described hereinbefore and shown in FIGS. 1, 2 and 4, the corresponding elements (i.e. elements which have the same function) will be indicated by the same numeral plus 100.

So the embodiments in FIGS. 8 and 9 show a holder 107: this holder can be moved up and down by means not shown, as these can be all kind of means, as a motor with an eccentric, a crank, but also a pneumatic driven plunger. The holder has in this example three cavities 130, in which a tube 106 is movable. Of course the movement of the tube 106 in the cavity 130 is restricted in downward direction by stops 131 and 132.

The tube 106 which forms an air chamber, is closed at the upper side by a transducer in the form of a microphone 117 and on the other side by a membrane 133, to which a ball 134 has been fixed. The microphone has a two-core cable 121 which leads to an electronic device 22 as described hereinbefore.

When using this apparatus the egg 1 is made to rotate around its axis of symmetry 105 and it is taken care that the holder 107 will make a vertical movement so that the tubes 106 with the balls 134 will be moved down on the egg shell. The result will be that the air in the air chamber will begin to vibrate. This vibration signal will be transmitted by the two-core cable 121 to the hereinbefore described electronic device 22 and will therefore not be described further herein.

The difference between the apparatus shown in FIG. 8 and in FIG. 9 is that the apparatus shown in FIG. 9 is more sophisticated. First of all the three tubes 106 are placed in a vertical position so that their setting in the cavities 130 will be smooth. Further in the embodiment of FIG. 9 the tubes 106 are influenced by a small spring 135, so that undesirable vibrations will not occur.

The apparatus according to FIG. 9 has in relation to the apparatus according to FIG. 8 the benefit that it gives a reliable signal and secondly that it is easier to produce such an apparatus.

It may readily be observed that when it comes to measuring the eggs that are transported in several rows on an egg conveyor it will be possible to build out the apparatus described above to an installation comprising a number of apparatuses, which individually, or in one or more groups, can be moved along so that they follow the eggs along a certain distance. Thus each apparatus can carry out a complete measurement of its particular egg, before the apparatus is brought back to repeat its measuring of a new egg on the conveyor.

The procedure and apparatus according to the invention have the following basic differences in relation to the known methods and apparatuses:

1. Continuous force during the measuring time;
2. Counting pre-determined kind of oscillations;
3. Comparing with preset parameters.

What I claim is:

1. A process for the examination of eggs to determine the presence of cracks or holes in the egg shell comprising the steps of: elastically attaching one end of a probe comprising a hard rod or tube to a holder to hold the probe in an initial position at a distance above an egg, effecting a continuous force in a pressure chamber on the holder to force the probe to strike against the egg on a portion of the probe at a distance of between 15% and 35% of the total length of the probe from a free end thereof to elastically deform the egg shell, subjecting the egg to an examination comprising repeatedly creating an elastic deformation of the egg shell, whereupon the resilience of the egg shell causes the shell to return to its original shape and throw back the probe several times with decreasing oscillations to effect a bouncing movement of the probe against said egg shell, converting the oscillations of the probe to electrical signals, measuring the electrical signals of each of the probe's oscillations, and repeating the examination a given number (n) of times evenly around the said egg's axis of symmetry.

2. A process according to claim 1, further comprising continuously rotating the egg around an axis of symmetry during the examinations.

3. A process according to claim 1 or 2, wherein several sections of the egg's shell along an axis of symmetry of the egg are concurrently examined and wherein the number of oscillations of each individual section are counted and registered individually and the lowest value among the (n) examinations times the number of sections is compared against a parameter value.

4. A process according to claim 1, wherein the decreased oscillations of the probe are measured and transduced into an electrical signal and further comprising amplifying the signal, comparing the signal to a reference value to obtain an output, reshaping the output to digital counting impulses, counting the impulses, transferring and storing the impulses in a computer concurrently with the results of the other examinations on the egg and determining the lowest value in the computer.

5. A process according to claim 1, wherein the measuring of electrical signals comprises measuring signals corresponding to the amplitude and duration of each of the probe oscillations and counting the number of oscillations that exceed a predetermined amplitude and duration.

6. An process according to claim 5, wherein the counted number in all repeated examinations on one egg are compared to each other and a predetermined value.

7. A process for the examination of eggs to determine the presence of cracks or holes in the egg shell comprising the steps of: at least partly closing a top side of a tubular probe with a microphone, at least partly closing the probe at a bottom side by a membrane to which a ball is fixed, freely mounting the probe in a cavity of a vertically movable holder and subjecting the holder to a continuous force directed at the egg's shell to force the probe down form an initial position at a distance from the egg shell to strike against the shell to elastically deform same, whereupon the resilience of the egg shell causes the shell to return to its original shape and throw back the probe several times with decreasing oscillations to effect a bouncing movement of the probe against said egg shell, thereby producing acoustic vibrations in the tubular probe, converting an acoustic signal from the microphone to electrical signals, measuring electrical signals of each of the probe's oscillations, and repeating the examination a given number (n) or times evenly around the egg's axis of symmetry.

8. A process according to claim 7, further comprising continuously rotating the egg around an axis of symmetry during the examinations.

9. A process according to claim 7 or 8 wherein several sections of the egg's shell along an axis of symmetry of the egg are concurrently examined and wherein the number of oscillations of each individual section are counted and registered individually and the lowest value along the (n) examinations times the number of sections is compared against a parameter value.

10. A process according to claim 7, wherein the decreased oscillations of the probe are measured and transduced into an electrical signal and further comprising amplifying the signal, comparing the signal to a reference value to obtain an output, reshaping the output to digital counting impulses, counting the impulses, transferring and storing the impulses in a computer concurrently with the results of the other examinations on the egg and determining the lowest value in the computer.

11. A process according to claim 7, wherein the measuring of electrical signals comprises measuring signals corresponding to the amplitude and duration of each of the probe oscillations and counting the number of oscillations that exceed a predetermined amplitude and duration.

12. The process according to claim 11, wherein the counted number in all repeated examinations on one egg are compared to each other and a predetermined value.

13. An apparatus for the examination of eggs to determine the presence of cracks or holes in an egg shell, comprising a base for receiving an egg including revolving rollers to rotate the egg around an axis of symmetry, a probe, means attaching the probe to a holder at a distance above the egg, means for setting the holder in motion to successively bounce the probe against the egg shell to cause an elastic deformation of the shell, transducing means connected to the probe for converting the probe's bouncing movement to an electrical signal and means for processing the signal from the transducing means, wherein the probe comprises a glass tube, wherein the attaching means comprises rubber chocks attaching one end of the tube to the holder for vertical and horizontal suspension and cushioning of the tube, and wherein the means attaching the probe positions same to strike against the egg shell within an area of the tube that is situated at a distance of between 15% and 35% of the total length of the glass tube from its free end.

14. An apparatus for the examination of eggs to determine the presence of cracks or holes in an egg shell, comprising a base for receiving an egg including revolving rollers to rotate the egg around an axis of symmetry, a probe, means attaching the probe to a holder at a distance above the egg, means for setting the holder in motion to successively bounce the probe against the egg shell to cause an elastic deformation of the shell, transducing means connected to the probe for converting the probe's bouncing movement to an electrical signal and means for processing the signal from the transducing means, wherein the probe comprises a tube connected one end to the holder and closed by a microphone, a membrane at least partly closing the other end of the tube and a ball fixed thereto, and means for moving the holder up and down.

15. An apparatus according to claim 14, wherein the holder is U-shaped, and the tube is oriented at right angles to the holder, and the mass of the tube is insignificant in comparison with the mass of the holder.

16. An apparatus for the examination of eggs to determine the presence of cracks or holes in an egg shell, comprising a base for receiving an egg including revolving rollers to rotate the egg around an axis of symmetry, a probe, means attaching the probe to a holder at a distance above the egg, means for setting the holder in motion to successively bounce the probe against the egg shell to cause an elastic deformation of the shell, transducing means connected to the probe for converting the probe's bouncing movement to an electrical signal and means for processing the signal from the transducing means, wherein the transducing means is connected to the one end of the probe, wherein the probe comprises a tube and wherein the holder is U-shaped, and the tube is oriented at right angles to side pieces of the holder, and the mass of the tube is insignificant in comparison with the mass of the holder.

17. An apparatus for the examination of eggs to determine the presence of cracks or holes in an egg shell, comprising a base for receiving an egg including revolving rollers to rotate the egg around an axis of symmetry, a probe, means attaching the probe to a holder at a distance above the egg, means for setting the holder in motion to successively bounce the probe against the egg shell to cause an elastic deformation of the shell, transducing means connected to the probe for converting the probe's bouncing movement to an electrical signal and means for processing the signal from the transducing means and means fixing the holder to the base comprising a laminated spring, an elastically deformable compressed air chamber between the holder and the base, an air pulsator and a vacuum escape valve fitted between the air pulsator and a vacuum escape valve fitted between the air pulsator and the air chamber via an air distribution chamber in the base.

18. An apparatus according to claim 17, further comprising several probes positioned to strike simultaneously on different sections of the egg shell.

19. An apparatus according to claim 17, further comprising a plurality of probes and holders and comprising compressed air chambers for the individual holders linked together by a common air distribution chamber.

* * * * *